US011311369B2

(12) United States Patent
Hristov et al.

(10) Patent No.: US 11,311,369 B2
(45) Date of Patent: Apr. 26, 2022

(54) DELIVERY SLEEVE

(71) Applicant: MENTOR WORLDWIDE LLC, Irvine, CA (US)

(72) Inventors: Krasimira Hristov, Hillsborough, NJ (US); Clifford Dwyer, Weston, FL (US); James Fleming, Bethlehem, PA (US); Robert Tannhauser, Bridgewater, NJ (US); Leo Kriksunov, Ithaca, NY (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 0 days.

(21) Appl. No.: 15/913,438

(22) Filed: Mar. 6, 2018

(65) Prior Publication Data
US 2019/0274817 A1 Sep. 12, 2019

(51) Int. Cl.
*A61F 2/12* (2006.01)
*A61B 17/34* (2006.01)
*A61F 2/00* (2006.01)
*A61B 17/00* (2006.01)

(52) U.S. Cl.
CPC ............ *A61F 2/12* (2013.01); *A61B 17/3468* (2013.01); *A61B 2017/00792* (2013.01); *A61B 2017/00796* (2013.01); *A61F 2/0095* (2013.01)

(58) Field of Classification Search
CPC .................. A61F 2/12; A61B 17/3421; A61B 17/3423–3429; A61B 1/015
See application file for complete search history.

(56) References Cited

U.S. PATENT DOCUMENTS

| 4,035,850 | A | | 7/1977 | Cresswall |
| 4,955,906 | A | | 9/1990 | Coggins et al. |
| 5,201,779 | A | | 4/1993 | Shiao |
| 5,279,539 | A | | 1/1994 | Bohan et al. |
| 5,549,679 | A | | 8/1996 | Kuslich |
| 5,723,006 | A | | 3/1998 | Ledergerber |
| 5,728,065 | A | * | 3/1998 | Follmer ................ A61M 25/10 |
| | | | | 604/96.01 |
| 6,605,093 | B1 | | 8/2003 | Blake |
| 8,182,459 | B2 | * | 5/2012 | Dann ............... A61B 17/00234 |
| | | | | 604/175 |

(Continued)

FOREIGN PATENT DOCUMENTS

CN 2897165 Y 5/2007
CN 208552129 U 3/2019
(Continued)

OTHER PUBLICATIONS

PCT Notification of Transmittal of the International Search Report and International Search Report of International Application No. PCT/IB2019/051820 dated Jun. 18, 2019, 8 Pages.
(Continued)

*Primary Examiner* — Jerrah Edwards
*Assistant Examiner* — Christine L Nelson
(74) *Attorney, Agent, or Firm* — Etan S. Chatlynne; Roberts Calderon Safran & Cole P.C.

(57) ABSTRACT

An implant-delivery sleeve may comprise an enclosure having at least one opening and at least one vent conduit. The vent conduit may extend along a surface of the enclosure to assist in removing fluids (e.g., blood and air) from the tissue pocket to facilitate implantation of the implant.

20 Claims, 5 Drawing Sheets

(56) References Cited

U.S. PATENT DOCUMENTS

| | | |
|---|---|---|
| 8,211,173 B2 | 7/2012 | Keller et al. |
| 8,409,279 B2 | 4/2013 | Freund |
| 8,641,758 B1 | 2/2014 | Anderson et al. |
| 9,414,941 B2 | 8/2016 | Placik et al. |
| 10,105,213 B2 | 10/2018 | Weinzweig |
| 2002/0091443 A1 | 7/2002 | Yoon |
| 2004/0225278 A1 | 11/2004 | Poole et al. |
| 2005/0080430 A1 | 4/2005 | Wright, Jr. et al. |
| 2007/0276484 A1 | 11/2007 | Abell et al. |
| 2008/0126119 A1 | 5/2008 | Sirohey et al. |
| 2008/0167606 A1 | 7/2008 | Dann et al. |
| 2009/0030400 A1 | 1/2009 | Bose et al. |
| 2009/0204107 A1 | 8/2009 | Keller et al. |
| 2011/0082546 A1 | 4/2011 | Freund |
| 2014/0148901 A1 | 5/2014 | Anderson et al. |
| 2014/0228951 A1 | 8/2014 | Zochowski |
| 2014/0249510 A1 | 9/2014 | Koblish et al. |
| 2014/0350462 A1 | 11/2014 | Ataollahi et al. |
| 2015/0032208 A1 | 1/2015 | Preissman |
| 2016/0374720 A1 | 12/2016 | Anderson et al. |
| 2017/0007295 A1* | 1/2017 | Geisz ............... A61B 17/3421 |
| 2017/0020500 A1* | 1/2017 | Taylor ............. A61B 17/00234 |
| 2017/0303905 A1 | 10/2017 | Wilson |
| 2018/0126119 A1 | 5/2018 | McNiven et al. |
| 2019/0274818 A1 | 9/2019 | Hristov et al. |
| 2019/0274819 A1 | 9/2019 | Graf et al. |

FOREIGN PATENT DOCUMENTS

| | | |
|---|---|---|
| EP | 2 630 927 A2 | 8/2013 |
| WO | 2010/099541 A1 | 9/2010 |
| WO | 2010/126462 A1 | 11/2010 |
| WO | 2012177587 A1 | 12/2012 |
| WO | 2017/213716 A1 | 12/2017 |
| WO | 2019/171300 A1 | 9/2019 |

OTHER PUBLICATIONS

Shaa'Ista Ameen, 'No-Touch' Breast-Implant Insertion Device, Submitted to the University of Cape Town, Faculty of Health Sciences, Department of Human Biology, University of Cape Town, Date of Submission: Jan. 1, 2016, URL: https://open.uct.ac.za/bitstream/handle/11427/20491/thesis_hsf_2016_ameen_shaa_039_ista.pdf?sequene=1 [retrieved on Feb. 27, 2018], pp. 74-76.

PCT Notification of Transmittal of the International Search Report and the Written Opinion of the International Searching Authority, or the Declaration for International Application No. PCT/IB2021/055927 dated Oct. 4, 2021, 6 pages.

* cited by examiner

DELIVERY SLEEVE

CROSS-REFERENCE TO CO-PENDING APPLICATIONS

This application is a counterpart of U.S. patent application Ser. No. 15/913,463, filed Mar. 6, 2018, and Ser. No. 15/913,484, filed Mar. 6, 2018, which are incorporated by reference herein in their entirety.

FIELD

The subject matter disclosed herein relates to devices and methods for delivering implants into a subject.

BACKGROUND

Tapered flexible sleeves, such as that marketed under the brand name, KELLER FUNNEL®, may be used as a delivery device for implanting a silicone-gel breast implant into a subject. These sleeves permit delivery of the implant through an incision that is shorter than it would need to be if the sleeve were not used. These sleeves may also lower the likelihood of introducing contaminants, e.g., microorganisms, into the subject through the incision because they minimize the amount of contact between the implant, surgeon's hands, and subject's tissue.

SUMMARY

An implant-delivery sleeve is disclosed. The implant delivery sleeve may assist in providing an implant, e.g., a tissue implant, such as a breast implant, into a tissue pocket of a subject, e.g., a human female patient. The implant-delivery sleeve may comprise an enclosure, which may be fabricated from, e.g., vinyl or elastomeric rubber, having at least one opening, e.g., a single opening or two openings, and at least one vent conduit, e.g., a single vent conduit or two vent conduits. The opening may be sized to permit passage of an implant therethrough. The vent conduit may extend along a surface of the enclosure. Further, the vent conduit may include a first end and a second end. The second end may be disposed proximate to the opening. In some embodiments, the entire vent conduit may be disposed within the enclosure. However, in some embodiments, the second end may be disposed outside the enclosure. Further, in some embodiments, a portion of the vent conduit may be disposed through a wall of the enclosure. Alternatively, in some embodiments, the entire vent conduit may be disposed outside the enclosure. In some embodiments, a segment of the vent conduit may extend away from the opening. For example, a segment connected to the second end may extend away from a longitudinal axis of the enclosure. In some embodiments, the first end of the vent conduit may be attached to an inner surface of the enclosure. Alternatively, in some embodiments, the first end of the vent conduit may be attached to an outer surface of the enclosure.

The delivery sleeve may further include a vent port, which may be disposed through a wall of the enclosure. The first end of the vent conduit may be attached to the vent port. The vent conduit may have a cross-sectional shape of a square, rectangle, ellipse, or circle.

In some embodiments, a channel may be disposed within a surface of the enclosure that may be or may function as the vent conduit. That is, in some embodiments, the vent conduit may include a channel disposed within a surface of the enclosure. Further, the vent conduit may include a corrugated surface.

In various alternative embodiments, the enclosure may be porous, the enclosure may include a handle, and/or an ampule containing a fluid (e.g., a lubricant) may be disposed on an inner surface of the enclosure.

As used herein, the terms "opening" and "port" each refer to a void (e.g., hole) through a wall or a membrane. Although the written description and figures present openings and ports as being round and having a diameter, it should be understood that an opening may be non-circular, e.g., square or triangular. In such instances, the diameters set forth herein for circular openings may be considered widths of non-circular openings. Accordingly, disclosure of a circular opening having a diameter of approximately three inches should be understood as also disclosing, for example, a rectangular opening having a width of approximately three inches.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
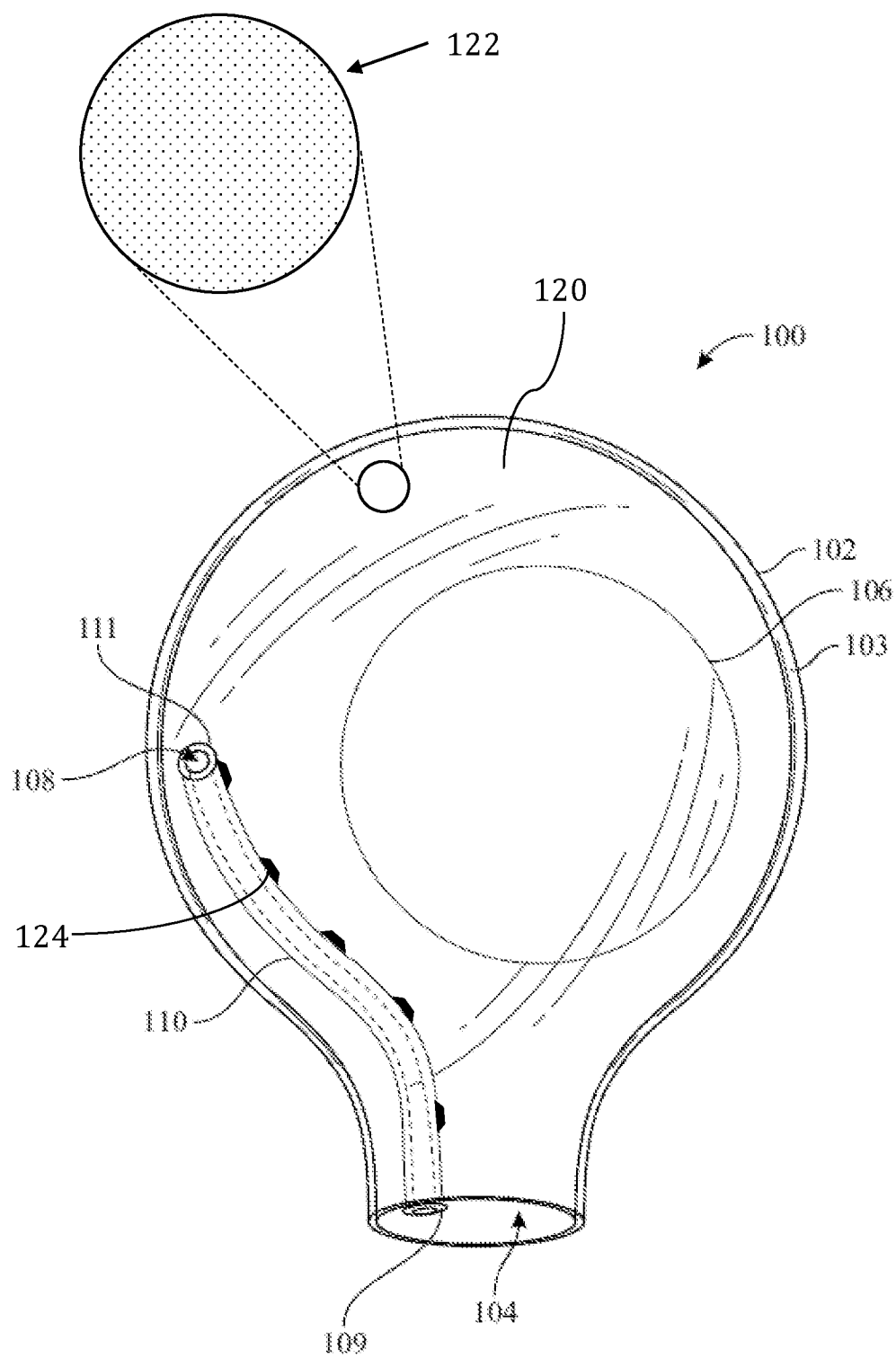
FIG. 1 depicts a delivery sleeve.

FIG. 1 shows an exemplary embodiment of a delivery sleeve 100. Delivery sleeve 100 may include a thin-walled enclosure 102 with an opening 104. An implant 106, e.g., a silicone-gel breast implant, may be provided within enclosure 102. Enclosure 102 may be fabricated by any suitable process, e.g., blow molding or sealing two sheets of a suitable material, e.g., vinyl, together to form a seal 103. A manufacturer of sleeve 100 may provide a sterilized and packaged product that includes enclosure 102 with implant 106 disposed therein. Alternatively, a manufacturer of sleeve 100 may provide a sterilized and package product that includes enclosure 102 but excludes implant 106 such that a medical professional, e.g., surgeon, would provide implant 106 and dispose implant 106 within enclosure 102. Opening 104 may have a diameter that approximates a width of an incision through which implant 106 is to be inserted into a subject. For example, opening 104 may have a diameter between approximately one inch and five inches. In some embodiments, opening 104 may have a diameter of approximately two inches. Although implant 106 may have a diameter greater than the diameter of opening 104, implant 106 may nonetheless be squeezed through opening 104 because implant 106 typically has a high degree of flexibility from being fabricated from a silicone gel or a saline solution encapsulated into a thin elastomeric shell.

Breast implants, such as implant 106, typically have a diameter ranging from between approximately three inches and eight inches. Implants are typically referred to by their diameter, e.g., "a five-inch implant," and such diameters correspond to a diameter of the widest cross section of the implant that is parallel to the base of the implant. Silicone-gel implants are flexible and pliable, and may be squeezed considerably to constrain the implant in a configuration such that the diameter of the implant may be constricted considerably, e.g., on the order of between approximately two times and ten times. For example, if implant 106 is a "three-inch implant" the portion that is three inches may be squeezed to constrict that portion down to a width of, e.g., 1.5 inches. Once the constrictive forces are removed, the portion recovers its original shape having a three-inch diameter.

Determination of the diameter of opening 104 may depend on the following design inputs. Sleeve 100 should assist in delivering implant 106 to a tissue pocket. Further, the access incision to the tissue pocket should be as small as possible taking into account the procedural requirements that 1) the implant 106 must fit through the incision; 2) the incision should be as small as possible to minimize scarring; and 3) the incision should not be so small that the implant causes the incision to rip or widen. Accordingly, opening 104 may be sized to have a diameter or width that is, at its smallest, approximately equal to the smallest width to which implant 106 may be constricted and, at its largest, approximately equal to the length of the incision. Therefore, the diameter of opening 104 depends on the size of the implant being used. Taking into account figures provided above, opening 104 may range from approximately 0.3 inches to approximately five inches. So dimensioned, opening 104 is configured or sized to permit passage of implant 106 therethrough.

Although FIG. 1 shows sleeve 100 as including a single opening, i.e. opening 104, it should be understood that additional openings may be provided through which implant 106 may pass, potentially while being squeezed. For example, it may include two openings, like the KELLER FUNNEL®, which has a frustoconical shape (e.g., tapered profile) that includes a first opening in a base and a second opening on a surface opposite the base.

In certain applications, it may be desirable to fabricate enclosure 102 from a material (e.g., one including vinyl or PVC) having a high elastic modulus (e.g., greater than approximately 1 gigapascal) such that opening 104 does not change size as implant 106 is squeezed therethrough, or a material (e.g., one including a high durometer elastomeric rubber, such as silicone rubber) having a moderate elastic modulus (e.g., between approximately 0.1 and 1 gigapascal) such that opening 104 may dilate a small amount (e.g., less than a 10% increase in diameter) as implant 106 is squeezed therethrough. This dilation may include deformation of enclosure 102 proximate opening 104 via elastic deformation, plastic deformation, or a combination thereof. In some embodiments, the material is selected so that passage of implant 106 through opening 104 results in reversible or temporary dilation of opening 104 corresponding to diameter increase ranging from 0% to 20%, such as 0, 3, 5, 10, and 20%.

Introduction of an implant, such as implant 106, using a sleeve, such as sleeve 100, into a surgical site, may also introduce air that may be contained within the sleeve, proximate the implant, into the surgical site. This air may pressurize and/or expand the surgical site, e.g., a tissue pocket, causing further and unnecessary trauma thereto. Further, fluids or air contained in the surgical site, e.g., tissue pocket, may be displaced by introduction of an implant therein. Ideally, such displacement should result in removing the air and fluid from within the tissue pocket to outside the tissue pocket, thereby facilitating introduction of implant 106 therein while avoiding potential trauma to the tissue pocket caused by trapping and compressing the air and fluid in the tissue pocket with implant 106. Simply put, by removing air and fluid from within the tissue pocket as implant 106 is introduced therein, there is more room for implant 106 to be disposed therein without causing trauma. Indeed, the size of implant 106 is determined based on the size of the tissue pocket, typically excluding the volume of fluid or air disposed therein.

Figure 2:
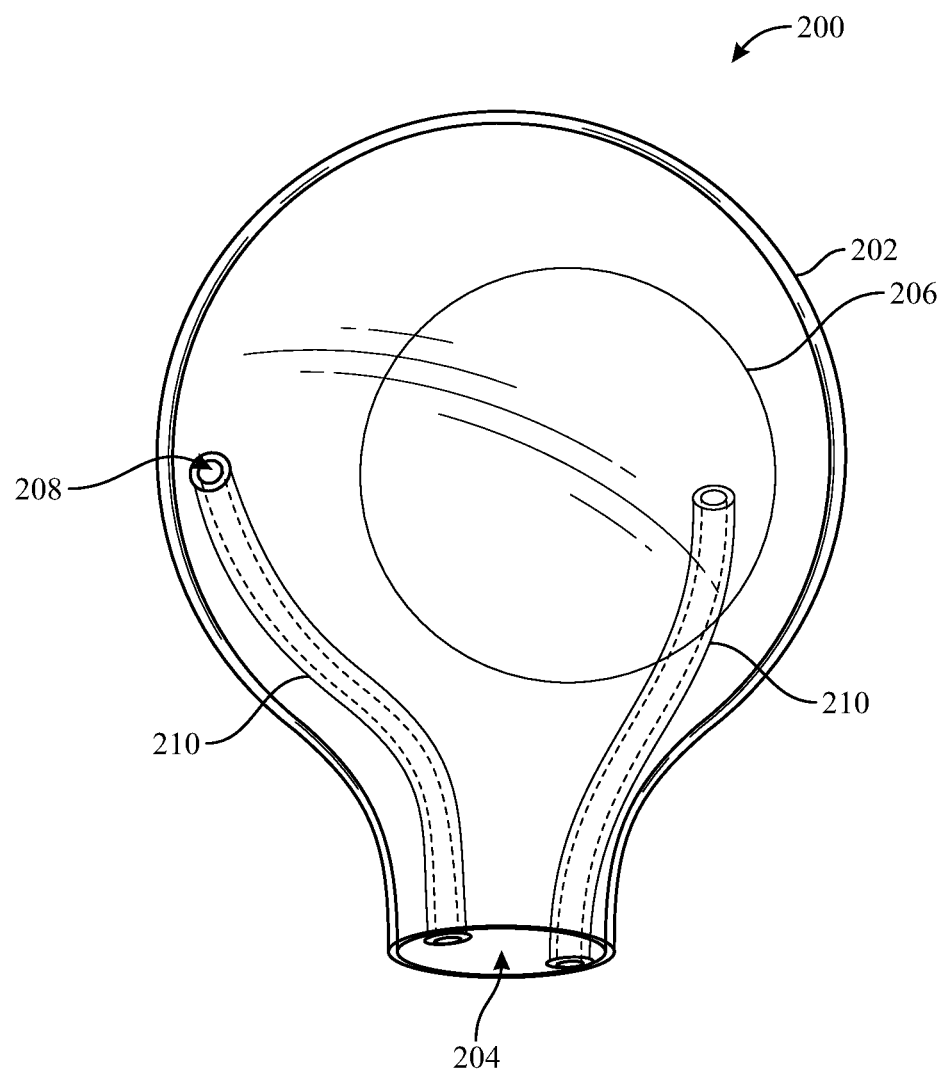
FIG. 2 depicts a first alternative embodiment of a delivery sleeve.

Based on the foregoing, a delivery sleeve may be provided with features that allow air and/or fluids within the enclosure to be vented out of the enclosure Further, a delivery sleeve may alternatively or additionally be provided with features that allow air and/or fluids to be vented out of the tissue pocket as an implant is introduced therein. Returning to FIG. 1, delivery sleeve 100 includes a vent port 108 disposed through enclosure 102. As shown, vent port 108 has a circular profile, but it may alternatively have a profile that is, e.g., square, rectangular, elliptical, or irregular. Further, it may simply be a slit, or a valve, such as an X-fragm valve. Vent port 108 should be relatively small as compared to opening 104 because it should permit passage of air and/or liquid therethrough, but it should prevent passage of implant 106 therethrough, even when implant 104 is deformed or squeezed. Thus, the width or diameter of vent port 108 should be at least approximately twenty times less than the diameter of implant 106. Therefore, for a three-inch implant, vent port 108 should have a diameter of approximately 0.15 inches or less. For a seven-inch implant, vent port 108 should have a diameter of approximately 0.35 inches or less. In various embodiments, e.g., as shown in FIG. 2 on sleeve 200, two or more vent ports 204 may be provided. The number of vent ports 208 may be inversely proportional to the size of each vent port 204. Accordingly, for example, two vent ports 208 may be provided having a diameter of approximately 0.4 inches, five vent ports may be provided having a diameter of approximately 0.3 inches, and 10 vent ports may be provided having a diameter of approximately 0.2 inches. Miniature vents or pores, which may be smaller than a tenth of an inch in diameter, or microscopic, may also be provided in larger numbers. For example, enclosure 102 may be fabricated from a breathable and porous material 120 (FIG. 1) having at least 100 pores 122 that are at least 0.001 inches in diameter. In those embodiments that include multiple vent ports, the multiple vent ports may be spread evenly or randomly about the sleeve. In some embodiments, the multiple vent ports may be concentrated together on a location of the sleeve. In some embodiments, they may be disposed in a line or in a pattern or shape, such as a circle. In some embodiments a first vent port in the line may originate proximate the opening (e.g., 104 or 204) and extend away therefrom.

In use, a surgeon squeezes enclosure 102 to compress it and advance implant 106 through opening 104, which could block air and/or fluid contained in the tissue pocket from venting via vent port 108. Accordingly, implant delivery sleeve 100 may additionally include a vent conduit, e.g., vent conduit 110, that may resist compression forces in order to maintain a space through which air or fluid may pass. Vent conduit 110 may originate proximate to vent port 108 and terminate proximate to opening 104 by including a first end 111 disposed proximate to vent port 108 and a second end 109 disposed proximate to opening 104. For example, as shown in FIG. 1, first end 111 may be connected to vent port 108 and second end 109 may be disposed within opening 104. However, it should be understood that alternative positions of first end 111 and second end 109 may accomplish similar or additional advantages relating to permitting the passage air and/or fluid. For example, first end 111 may be disposed within enclosure 102, removed or spaced from vent port 108. First end 111 may be disposed outside enclosure 102, such that conduit 110 passes through vent port 108. Second end 109 may be disposed within enclosure 102, spaced above opening 104. Second end 109 may be disposed outside enclosure 102 such that conduit 110 passes through opening 104. Vent conduit 110 may be disposed entirely within enclosure 102. Alternatively, vent conduit 110 may be disposed entirely outside of enclosure 102 (e.g., refer to FIGS. 3 and 4). Sleeve 200 may include vent conduits 210 disposed relative to enclosure 202 in a similar manner.

As shown in FIGS. 1 and 2, vent conduits 110 and 210 have a tubular form. However, the form need not be tubular. For example, a channel (e.g., slit or groove) may be formed in an inner wall of enclosure 102. This channel may originate proximate to port 108 and terminate proximate to opening 104. Accordingly, vent conduits 110 and 210 may be any structure that prevents an implant from occluding gases (e.g., air) or liquids (e.g., blood) escaping form a tissue pocket while an implant is being inserted therein.

In those embodiments that include multiple vent ports disposed in a pattern, such as a line, a vent conduit (e.g., 110 or 210) may be disposed along the pattern, e.g., along a path defined by the line. In further embodiments, holes may be disposed along and through the conduit in fluid communication with the vent ports. In these further embodiments, the conduit may have structure akin to a soaker hose. Alternatively, the conduit may include a longitudinal groove or slit that is/are in fluid communication with the ports along the pattern, e.g., line.

Vent conduit 110 and vent conduits 210 may be rigid or semi-rigid in nature, e.g., fabricated from a high-durometer or thick-walled tubing, such as PVC tubing, nylon tubing or Tygon® tubing. Additionally, the vent conduits may include a corrugated surface 124 (FIG. 1) to further resist deformation that could block flow therethrough. Thus, while a surgeon squeezes an enclosure (e.g., 102 or 202) to advance an implant (e.g., 106 or 206) through an opening (e.g., 104 or 204) and into a tissue pocket, air and/or liquid may pass through a vent conduit (e.g., 110 or 210) and out of a vent port (e.g., 108 or 208).

As shown in FIGS. 1 and 2, vent conduits 110 and 210 originate within opening 104 and 204 and terminate within the enclosures 102 and 202, at port 108 and 208. However, in some embodiments, and with reference to enclosure 100, one or more vent conduits may pass through the wall of enclosure 102, e.g. through vent port 108, to terminate outside of the enclosure. In some embodiments, one or more of these vent conduits, or additional vent conduits, may originate outside of enclosure 102 and pass through the wall of enclosure 102, e.g., through vent port 108, to terminate within enclosure 102. In some embodiments, one or more vent conduits 110 may originate within opening 104 and terminate within enclosure 102. In some embodiments, one or more vent conduits 110 may originate outside enclosure 102 and pass through opening 104 to terminate within enclosure 102, e.g., proximate to vent port 108. In some embodiments, second end 109 of conduit 110 may include an elbow. For example, a segment of vent conduit 110 may pass from within enclosure 102, through opening 104, then bend away from opening 104 at an angle, e.g., a right angle, and terminate at second end 109, which may minimize the likelihood that implant 106 may block second end 109 of conduit 110 as the implant exits through opening 104. In some embodiments, one or more vent conduits may be bifurcated such that the conduit may terminate both inside and outside of enclosure 102. Alternatively, a bifurcated vent conduit may originate outside opening 104 and terminate both within and outside of enclosure 104. In those embodiments in which a conduit (e.g., 110 or 210) passes form within an enclosure (e.g., 102 or 202) and in which a vent port (e.g., 108 or 208) is disposed proximate an opening (e.g., 104 or 204) of the enclosure, the vent conduit may be oriented transversely to force provided by a surgeon squeezing the enclosure, which may further resist deformation caused by a surgeon squeezing the enclosure.

Figure 3:
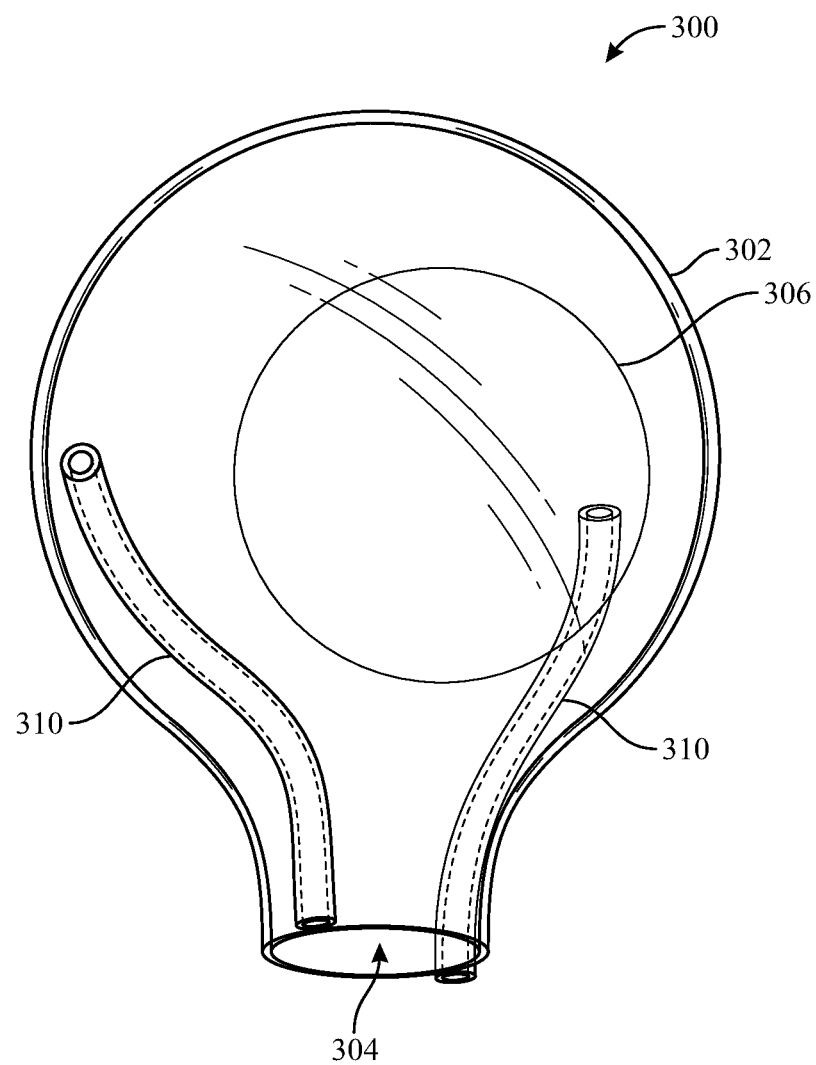
FIG. 3 depicts a second alternative embodiment of a delivery sleeve.

FIG. 3 shows another embodiment demonstrating alternative positioning of vent conduits. Implant 300 may include one or more vent conduits 310 disposed proximate to but outside enclosure 302. For example, vent conduits 310 may be attached to an outer surface of enclosure 302. Correspondingly, enclosure 302 need not include a vent port (e.g., akin to vent port 108) disposed therethrough.

Figure 4:
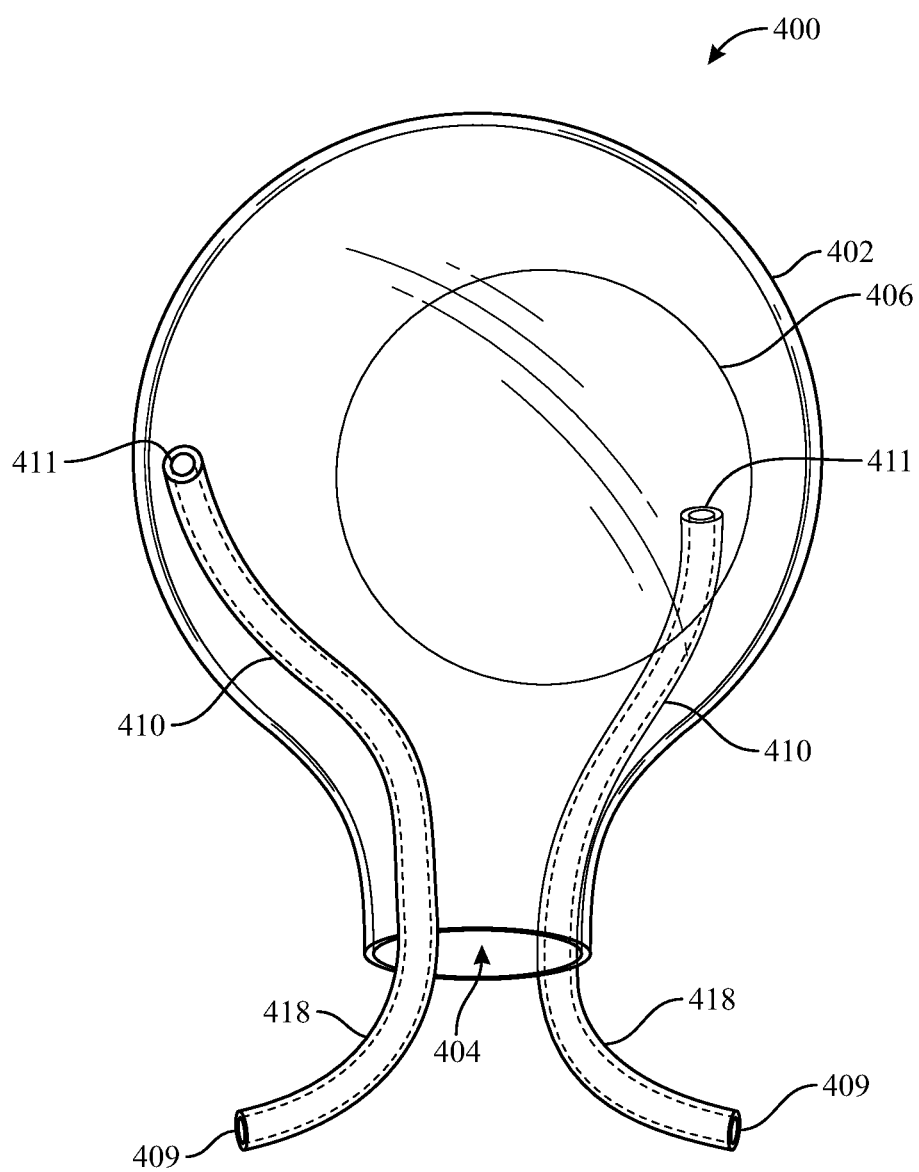
FIG. 4 depicts a third alternative embodiment of a delivery sleeve.

FIG. 4 reflects another embodiment of the delivery sleeve. Delivery sleeve 400 may include enclosure 402, opening 404, and at least one vent conduit 410 disposed outside of enclosure 402, e.g., attached thereto. As shown, delivery sleeve 400 lacks a vent port, however one may be included. Vent conduit 410 may include a first end 411 disposed above opening 404 and a second end 409 disposed below opening 404. Second end 409 and a segment 418 of conduit 410 connected thereto may be bent away from opening 404, e.g., in a curved or angled configuration that extends away from a longitudinal axis of enclosure 402 passing through opening 404, which may help prevent implant 406 from blocking second end 409 as implant 406 is extruded out of opening 404. Accordingly, in use, second end 409 and segment 418 would be the first part of sleeve 400 to be inserted into the tissue pocket.

As shown in FIGS. 3 and 4, vent conduits 310 and 410 have a tubular form. However, the form need not be tubular. For example, a channel (e.g., slit or groove) may be formed in an outer wall of the enclosure (e.g., 302 and 402). This channel may extend from above the opening (e.g., 304 and 404) and terminate proximate to the opening. Accordingly, vent conduits 310 and 410 may be any structure that prevents an implant from occluding gases (e.g., air) or liquids (e.g., blood) escaping form a tissue pocket while an implant is being inserted therein.

The vent conduits (e.g., 110, 210, 310, and 410) may have inner diameters of between approximately 0.1 and 0.8 inches. For example, each vent conduit may have a diameter of approximately 0.5 inches. The number of vent conduits may be inversely proportional to the inner diameter of each vent conduit. Accordingly, for example, two vent conduits 210 may be provided having an inner diameter of approximately 0.4 inches, five vent conduits may be provided having a diameter of approximately 0.3 inches, and 10 vent conduits may be provided having a diameter of approximately 0.2 inches.

Figure 5:
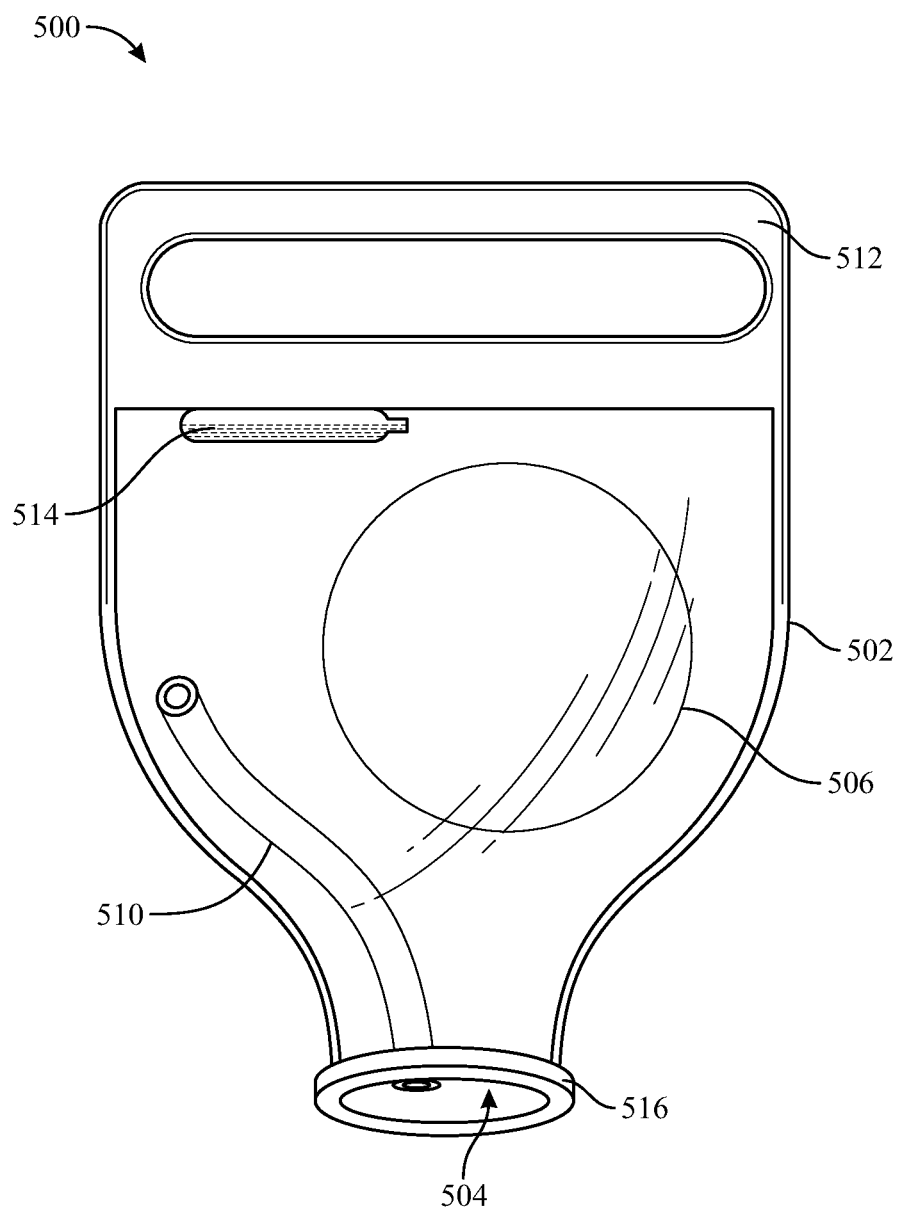
FIG. 5 depicts a fourth alternative embodiment of a delivery sleeve.

Implants having vent ports and/or vent conduits may additionally include other features that may assist a surgeon to deliver an implant with minimal trauma. For example, as shown in FIG. 5, sleeve 500 includes an enclosure 502, an opening 504, and a vent conduit 510. Implant 500 additionally includes a handle 512, a container 514, and a retainer ring 516.

Handle 512 may be an integral portion of enclosure 502 or it may be a separate component assembled thereto, disposed on an opposite end of enclosure 502 from opening 504. A surgeon may grasp handle 512 with one hand while squeezing enclosure 502 with another hand, which may provide the surgeon with greater control over the delivery than is possible using a sleeve that lacks a handle.

Container or ampule 514 may be disposed within enclosure 502. For example, ampule 514 may be connected to an internal surface of enclosure 502, or it may be embedded within the material of enclosure 502. A fluid, such as a lubricant (e.g., silicone or saline) or another fluid, such as a disinfectant solution, may be contained within ampule 514. A user may rupture ampule 514 to expose the inside of enclosure 502 and an implant, should one be disposed therein, to the fluid. In various embodiments, ampule 514 may be fabricated from a material that may be ruptured by squeezing without creating debris. For example, plastic ampules may be preferable over glass ampules.

A retainer ring 516 may be provided about opening 504. Retainer ring 516 may be fabricated from material having a greater stiffness or resilience than the material of enclosure 502. For example, retainer ring 516 may be a thick-walled o-ring fabricated from silicone rubber having an inner diameter approximately equal to the diameter of opening 504. The wall thickness of retainer ring 516 may be between approximately 0.5 inches and 2 inches. For example, opening 504 may have a diameter of approximately two inches, and retainer ring may 516 have an inner diameter of approximately two inches and a wall thickness of approximately one inch. Retainer ring 516 is thus capable of maintaining opening 504 in an open-circle configuration while allowing deformation of this configuration by a surgeon. Accordingly, retainer ring 516 assists in placing opening 504 through an incision and into a tissue pocket, and it helps avoid inadvertent removal of opening 504 from the tissue pocket. Furthermore, once ring 516 has been disposed into the tissue pocket, the surgeon may pull on handle 512, e.g., in a direction away from the tissue pocket, which transfers force to ring 516, causing the incision to open, which may ease delivery of implant 506 through opening 504.

In some embodiments, conduit 510 can pass through retainer ring 516, either through the annular space defined by the ring or through the ring itself. For example, in those embodiments where conduit 510 is disposed entirely outside enclosure 502, conduit 510 may pass through ring 516, between its inner and outer cylindrical surfaces.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometries, materials, dimensions, ratios, steps, and the like discussed above are illustrative. Accordingly, the claims should not be limited to the specific details of structure and operation set forth in the written description and drawings.

We claim:

1. An implant-delivery sleeve, comprising:
   an enclosure having an opening, a vent port disposed through the enclosure, and a vent conduit, wherein the opening is sized to permit passage of an implant therethrough and the vent conduit extends between the opening and the vent port along a surface of the enclosure, and
   wherein the enclosure is porous.

2. The implant-delivery sleeve of claim 1, wherein the vent conduit includes a first end disposed proximate to the vent port and a second end disposed proximate to the opening.

3. The implant delivery sleeve of claim 2, wherein the vent conduit is entirely disposed within the enclosure.

4. The implant delivery sleeve of claim 2, wherein a portion of the vent conduit is disposed through the vent port.

5. The implant delivery sleeve of claim 1, wherein the opening consists of a single opening.

6. The implant delivery sleeve of claim 5, further comprising a handle disposed opposite to the single opening.

7. The implant delivery sleeve of claim 2, wherein the second end is disposed outside the enclosure.

8. The implant delivery sleeve of claim 7, wherein the entire vent conduit is disposed outside the enclosure.

9. The implant delivery sleeve of claim 7, wherein the vent conduit further includes a segment connected to the second end that extends away from a longitudinal axis of the enclosure.

10. The implant delivery sleeve of claim 9, wherein the first end is attached to an inner surface of the enclosure.

11. The implant delivery sleeve of claim 9, wherein the first end is attached to an outer surface of the enclosure.

12. The implant delivery sleeve of claim 2, wherein the first end of the vent conduit is attached to the vent port.

13. The implant delivery sleeve of claim 2, wherein the conduit has a cross-sectional shape of a square, rectangle, ellipse, or circle.

14. The implant delivery sleeve of claim 2, wherein the enclosure is fabricated from vinyl or an elastomeric rubber.

15. The implant delivery sleeve of claim 2, wherein the vent conduit includes a channel disposed within a surface of the enclosure.

16. The implant delivery sleeve of claim 2, wherein the conduit includes a corrugated surface.

17. The implant delivery sleeve of claim 2, further comprising an ampule containing a fluid, the ampule disposed upon an inner surface of the enclosure.

18. The implant delivery sleeve of claim 1, wherein the enclosure comprises a material having an elastic modulus of between approximately 0.1 gigapascal and 1 gigapascal.

19. The implant delivery sleeve of claim 1, wherein the opening has a diameter of between approximately one inch and approximately five inches.

20. The implant delivery sleeve of claim 1, further comprising a breast implant disposed within the enclosure.

* * * * *